United States Patent [19]
Gellman et al.

[11] Patent Number: 5,563,057
[45] Date of Patent: Oct. 8, 1996

[54] METHOD FOR REFOLDING MISFOLDED ENZYMES WITH DETERGENT AND CYCLODEXTRIN

[75] Inventors: Samuel H. Gellman; David B. Rozema, both of Madison, Wis.

[73] Assignee: Wisconsin Alumni Research Foundation, Madison, Wis.

[21] Appl. No.: 332,188

[22] Filed: Oct. 31, 1994

[51] Int. Cl.$^6$ ............................ C12N 9/96; C07K 1/14
[52] U.S. Cl. ..................... 435/188; 530/412; 530/427
[58] Field of Search ................................ 435/188, 814; 530/412, 427

[56] References Cited

U.S. PATENT DOCUMENTS

| | | | |
|---|---|---|---|
| 4,511,502 | 4/1985 | Builder et al. | 530/417 |
| 4,677,196 | 6/1987 | Rausch et al. | 530/412 |
| 4,766,205 | 8/1988 | Ghosh-Dastidar | 530/402 |
| 4,923,967 | 5/1990 | Bobbitt et al. | 530/351 |
| 4,975,529 | 12/1990 | Frazier et al. | 530/399 |
| 5,136,027 | 8/1992 | Pope | 530/427 |

OTHER PUBLICATIONS

King (10 Apr. 1989) *Chem. Eng. News*, pp. 32–54.
N. K. Puri et al., Solubilization of growth hormone and other recombinant proteins from *Escherichia coli* inclusion bodies by using a cationic surfactant, 285 Biochem. J. 871–879 (1992).
J. I. Cleland, Impact of Protein Folding on Biotechnology in Proteins Folding In Vivo and In Vitro, American Chemical Society, Chapter 1 (1993).
Y. Pocker et al., The Catalytic Versatility of Erythrocyte Carbonic Anhydrase. III. Kinetic Studies of the Enzyme-Catalyzed Hydrolysis of p–Nitrophenyl Acetate, 6 Biochemistry 668–678 (1967).
P. A. Srere et al., The Citrate Condensing Enzyme of Pigeon Breast Muscle and Moth Flight Muscle, 17 CTA Chemica Scand. S129–S134 (1963).
C. H. Schein, Production of Soluble Recombinant Proteins in Bacteria, 7 Bio/Technology 1141–1147 (1989).
W. Zhi et al., Renaturation of citrate synthase: Influence of denaturant and folding assistants, 1 Protein Science 522–529 (1992).
F. A. O. Marsten, The purification of eukaryotic polypeptides synthesized in *Escherichia coli*, 240 Biochem J. 1–12 (1986).
J. I. Cleland et al., Cosolvent Assisted Protein Refolding, 8 Bio/Technology 1274–1278 (1990).
J. I. Cleland et al., Polyethylene Clycol Enhanced Protein Refolding, 10 Bio/Technology 1013–1019 (1992).
G. A. Bowden et al., The Effect of Sugars on β–Lactamase Aggregation in *Escherichia coli*, 4 Biotechnology Progress 97–101 (1988).
G. Zardeneta er al., Micelle–assisted Protein Folding, 267 The Journal of Biological Chemistry 5811–5816 (1992).
R. Schomaecker, et al., Interaction of Enzymes with Surfactants in Aqueous Solution and in Water–in–oil Microemulsions, 84 J. Chem. Soc. 4203–4212 (1988).
V. T. Liveri et al., Calorimetric investigation of the complex formation between surfactants and α–, β– and γ–cyclodextrins, 199 Thermochimica Acta 125–132 (1992).
U. R. Dharmawardana et al., A Surface Tension Method for Determining Binding Constants for Cyclodextrin Inclusion Complexes of Ionic Surfactants, 9 Langmuir 2258–2263 (1993).
M. Lee et al., Ability of Cyclodextrins to Inhibit Aggregation of β–Casein, 39 J. Agric. Food Chem. 17–21 (199).
M. E. Brewster et al., Use of 2–Hydroxypropyl–β–cyclodextrin as a Solubilizing and Stabilizing Excipient for Protein Drugs, 8 Pharmaceutical Research 792–796 (1991).
A. Cooper, Effect of Cyclodextrins on the Thermal Stabillity of Globular Proteins, 114 J. Am. Chem. Soc. 9208–9209 (1992).

*Primary Examiner*—David M. Naff
*Assistant Examiner*—Jon P. Weber
*Attorney, Agent, or Firm*—Quarles & Brady

[57] ABSTRACT

A method for refolding an enzyme from a misfolded configuration to a second native and active configuration is presented. The method comprises adding a linear alkyl detergent to a misfolded enzyme to form an enzyme-detergent complex. Then the enzyme-detergent complex is contacted with a cyclodextrin to allow the enzyme to assume a second active configuration. The misfolded enzyme may have been previously denatured by heat or by chemical means other than a detergent.

7 Claims, No Drawings

METHOD FOR REFOLDING MISFOLDED ENZYMES WITH DETERGENT AND CYCLODEXTRIN

This invention was made with United States government support awarded by National Science Foundation Grant #NSF Presidential Young Investigator Award #CHE 9157510 and National Institutes Of Health Grant No.: NIH First Award #GM 41825. The United States government has certain rights in this invention.

This research was made with United States government support awarded by the National Institutes of Health (NIH) Grant number GM41825. The United States government may have rights with respect to this invention.

FIELD OF THE INVENTION

The present invention relates to a method for refolding of a protein from a first inactive state to a second active state. One use of the invention would be in connection with recombinantly expressed proteins that have been expressed from cells in a misfolded configuration that renders them inactive.

BACKGROUND OF THE INVENTION

The ability to overproduce natural or modified proteins in genetically engineered cells has helped create an expanded biotechnology industry. While some proteins have been expressed in an active state, others have been expressed in an inactive, misfolded configuration. A number of attempts have been made to try to cause a refolding of a protein to an active configuration by adding a chemical. See e.g. J. Cleland, Protein Folding: In Vivo And In Vitro (ACS Series No. 526, Chapter 1) (1993); J. Cleland, et al. 10 Bio/Technology 1013–1019 (1992); C. Schein, 7 Bio/Technology 1141–1147 (1989); J. Cleland, et al., 8 Bio/Technology 1274–1278 (1990); G. Zardeneta et al., 267 J. Biol. Chem. 5811–5816 (1992); and U.S. Pat. No. 4,766,205. The disclosure of these publications and of all other publications referred to herein are incorporated by references as if fully set forth herein. Additives have included chaperone proteins, other types of proteins (e.g. bovine serum albumin), and several types of non-protein materials, including sucrose, glycerol, enzyme substrates (when the protein to be refolded is an enzyme), synthetic polymers, and detergents.

However, for some proteins renaturation of overproduced proteins remains problematic. Therefore, there still is a need to develop strategies for protein refolding that work with proteins resistant to refolding using conventional techniques.

SUMMARY OF THE INVENTION

In one aspect, the invention provides a method for refolding a protein from a first misfolded configuration where the protein is defective in a desired attribute to a second configuration where the protein is not defective in that attribute. The method comprises adding a detergent to the protein to form a detergent/protein complex. One then adds a cyclodextrin. This causes the detergent to be sequestered from the complex by the cyclodextrin and permits the protein to achieve the second configuration.

In a preferred embodiment, a denaturing step precedes the use of the detergent, the protein is an enzyme and the desired attribute is enzymatic activity. The denaturation step can involve a heating step or chemical denaturation. For example, heating proteins to 70° C. for at least ten minutes will usually suffice to denature a protein (albeit for some proteins heating for longer periods or at higher temperatures will be needed to denature the protein). In an even more preferred embodiment, the misfolded protein is at some point in the method (e.g. at the beginning) in a non-denaturing environment.

The detergent is amphiphilic, aggregate cooperative in water, and either anionic, cationic, zwitterionic or non-ionic.

In yet another embodiment, the protein is purified by a filtration step.

The preferred embodiment includes introduction of two low molecular weight agents to promote the adoption of a protein's native conformation under conditions that, in the absence of both additives, leads to misfolded protein. The detergent first forms a complex with the non-native protein. In a second step, cyclodextrin is added and slowly "strips" the detergent from the protein. Surprisingly, as it does so, it permits the adoption by the protein of the native state.

The objects of the invention therefore include providing:

(a) a method of the above kind for refolding an inactive protein into a native conformation; and (b) a method of the above kind that can be used with inexpensive materials.

These and still other objects and advantages of the present invention will be apparent from the description that follows. It should be understood that the following is merely a description of the preferred embodiments, and is not intended as a description of all possible embodiments. The claims should be looked to to determine the full scope of the invention.

DESCRIPTION OF THE PREFERRED EMBODIMENTS

EXAMPLE 1

We first proved that our system could prevent misfolding from a denatured state. 350 µl aliquots containing 1.4 µM carbonic anhydrase B ("CAB") (Sigma Biochemicals) in 23 mM Tris, pH 7.75, and, when indicated, 0.57 mM detergent, were heated to 70° C. for 6 minutes, and then allowed to cool 15 minutes. Then, 150 µl 16 mM aq. β-cyclodextrin, or 150 µl water, was added, to give final concentrations of 1.0 µM CAB, 0.4 mM detergent (when present) and 4.8 mM β-CD (when present). The resulting solutions were allowed to stand overnight before assay.

For "native protein" control experiments, the reaction solutions were assembled in the same way, but the heating step was omitted. For the "background" control experiments, the CAB was omitted. An activity assay, involving pNPAc ("p-nitrophenyl acetate") hydrolysis, was performed as reported in Y. Pocker et al., 6 Biochem. 668 (1967) and monitored via production of p-nitrophenolate (absorbance at 400 nm).

TABLE I

| Additives | Relative Initial Rate |
|---|---|
| NATIVE PROTEIN | |
| None | 1.00 |
| β-CD | 0.96 ± 0.04 |
| CTAB ($CH_3(CH_2)_{15}N(CH_3)_3 + Br^-$) | 0.89 ± 0.05 |
| CTAB; β-CD | 0.89 ± 0.04 |

TABLE I-continued

| Additives | Relative Initial Rate |
|---|---|
| BACKGROUND (No Enzyme) | |
| None (buffer only) | 0.01 ± 0.00 |
| β-CD | 0.02 ± 0.00 |
| CTAB | 0.01 ± 0.00 |
| AFTER HEATING | |
| None | 0.02 ± 0.00 |
| β-CD | 0.03 ± 0.00 |
| CTAB | 0.03 ± 0.01 |
| CTAB; β-CD | 0.81 ± 0.02 |

Light scattering measurements indicated that the protein had aggregated as a result of the heating and recooling (in the absence of detergent). When the heating was instead carried out in the presence of the detergent, cetyltrimethylammonium bromide (CTAB), no light scattering was detected in the cooled solution, but the enzyme was still essentially inactive. Thus, adding the detergent alone was insufficient to permit proper folding.

However, addition of cyclodextrin to the denatured protein-detergent complex solution after cooling, caused reactivation of the enzyme with a yield of 81% recovered activity.

The reactivated enzyme was then purified by a two step procedure. We first passed the materials through a 0.22 μm acetate filter to remove large protein aggregates (saving the protein passing through the filter), and then concentrated the protein with a 10,000 MW cut-off filter to remove the smaller detergent and cyclodextrin.

The resulting protein solution was identical to a solution containing non-denatured CAB at similar concentration, as judged by circular dichromism, intrinsic fluorescence, and specific activity.

pNPAc hydrolysis in the presence of β-CD alone, or CTAB alone, was well below the activity observed with the native CAB.

α-CD was essentially as effective as β-CD in the above test (e.g. 80% recovery of activity).

EXAMPLE II

We then took a sample of the protein from Example I which had been misfolded by simple heating and cooling, and successfully refolded the protein by adding detergent and cyclodextrin to the cooled inactive protein as follows: CTAB was added to 0.57 mM, and the solution was allowed to stand for 10 minutes. 150 μl of 16 mM aq. β-CD was added, to give final concentrations of 1.0 μM CAB, 0.4 mM CTAB, and 4.8 mM β-CD. The resulting solution was allowed to stand overnight before assay. 79% of the activity was recovered in this way.

EXAMPLE III

Citrate synthase ("CS") (Boehringer), 24 μM, was denatured for 1 hour in 6M guanidinium chloride containing 35 mM DTT. This solution was then diluted to give a solution containing 0.34 μM CS, 85 mM GdmCl, 0.5 mM DTT, 143 mM Tris-HCl, pH 8.0, 0.71 mM EDTA, and, when indicated, 0.57 mM detergent (70 μl aliquots). After 1 hour, these aliquots were further diluted with 30 μl 5.3 mM aq. β-CD or 30 μl water, to give final concentrations of 0.24 μM CS, 60 mM GdmCl, 0.35 mM DTT, 100 mM Tris-HCl, pH 8.0, 0.5 mM EDTA, and, when indicated, 0.4 mM detergent and 1.6 mM β-CD. These solutions were allowed to stand overnight before being subjected to the assay described in P. Srere, et al., 17 Acta. Chem. Scand. SI29 (1963), which was followed spectrophotometrically at 412 nm.

TABLE II

| Additives | Relative Initial Rate |
|---|---|
| NATIVE PROTEIN | |
| None | 1.00 |
| β-CD | 0.92 ± 0.09 |
| POE(10)L (CH$_3$(CH$_2$)$_{11}$(OCH$_2$CH$_2$)$_{10}$OH) | 1.08 ± 0.15 |
| POE(10)L; β-CD | 1.06 ± 0.09 |
| AFTER UNFOLDING AND DILUTION | |
| None | 0.02 ± 0.00 |
| β-CD | 0.01 ± 0.00 |
| POE(10)L | 0.01 ± 0.00 |
| POE(10)L; β-CD | 0.50 ± 0.06 |

EXAMPLE IV

We then took a sample from Example III, which had been misfolded by simple dilution of the guanidinium-denatured CS, and successfully refolded the protein by adding detergent and cyclodextrin to the inactive protein as follows: 15 minutes after dilution, POE(10)L was added to 0.86 mM, and the solution was allowed to stand for 45 minutes. 30 μl of 16 mM aq. β-CD was added, to give final concentrations of 0.24 μM CS, 0.6 mM POE(10)L, and 4.8 mM β-CD. The resulting solution was allowed to stand overnight before assay. 21% of the activity was recovered this way.

EXAMPLE V

Same as Example III, except α cyclodextrin was used in place of β-cyclodextrin. There was 29% recovery of the activity.

EXAMPLE VI

Same as Example III, except that the non-ionic detergent Triton X-100 was used, with 19% recovery. (β-CD)

THEORETICAL BASIS

Our research indicates that the detergent is being encased in the internal cavity of the cyclodextrin so as to thereby sequester the detergent from the protein. However, the process of "stripping" the detergent from the protein is such that proper refolding surprisingly occurs.

It should be appreciated that only the preferred embodiments have been described above. Thus, the claims should be looked to in order to judge the full scope of the invention.

For example, while α and β cyclodextrin have been specifically discussed, other cyclic glucose oligomers are intended to be within scope of the phrase "cyclodextrin (e.g. γ-cyclodextrin). Also included are cyclodextrins with a substitution on a glucose (e.g. ammoniocarboxylate derivatized β cyclodextrin), and cyclic oligomers of glucose with insertions in the chain such as β cyclodextrin epichlorohydrin co-polymer (Aldrich Chemical).

Further, a wide variety of protein denaturing chemicals are intended to be within the scope of the claims (e.g. urea).

Also, a wide variety of proteins (apart from just enzymes) such as hormones, interleukins, DNA-binding proteins, enzyme inhibitor proteins, metabolite-binding and nutrientbinding proteins, regulatory proteins, i.e., all globular proteins, should be suitable for use with this method.

Further, a wide variety of detergents should be useful (e.g. DTAB; CTAHS; TTAB; SDS; STS; SHS; Z3–14; Z3–16; lauryl maltoside; sarkosyl). In selecting a detergent and cyclodextrin to use with each other, we take into account (i) the size of the nonpolar portion of the detergent. α-CD is smaller than β-CD, and α-CD is capable of binding more strongly to detergents that have linear alkyl chains as their nonpolar portion. Thus, for example, α-CD does not as strongly bind the bulky p-t-octylphenyl nonpolar moiety of Triton X-100. β-CD, however, does bind this bulky group quite well and β-CD has proven to be an especially effective stripping agent for Triton X-100 and (ii) the solubility of the cyclodextrin; α-CD is considerably more soluble than β-CD.

The relative ratios of detergent, protein, and cyclodextrin can vary, but it preferred that the cyclodextrin/detergent ratio be between 2 to 10, and that the detergent be far in excess of the protein (e.g. a detergent protein ration of between 400 to 1500.

We claim:

1. A method for folding an enzyme from a first misfolded configuration where the enzyme is completely defective in enzymatic activity to a second, native and active configuration where the enzyme has enzymatic activity, and then at least partially purifying the enzyme, the method comprising:

adding a detergent having a linear alkyl non-polar portion to the enzyme to form a detergent-enzyme complex, where immediately prior to the addition of the detergent, the enzyme is in said first configuration;

contacting the detergent-enzyme complex with a cyclodextrin in an aqueous solution whereby the enzyme assumes the second active configuration; and then at least partially purifying the enzyme that is in the second active configuration by separating it from the detergent.

2. The method of claim 1, wherein the first configuration results from denaturing the enzyme.

3. The method of claim 2, wherein the denaturing is caused by a heating step, and cyclodextrin is added after a cooling step, the cooling step following the heating step.

4. The method of claim 2, wherein the denaturing is caused by the addition of a denaturing chemical other than a detergent.

5. The method of claim 1, wherein the cyclodextrin is α-cyclodextrin or β-cyclodextrin.

6. The method of claim 1, wherein the detergent is anionic, cationic, non-ionic or zwitterionic.

7. The method of claim 1, wherein the separation step comprises passing the enzyme that is in the second active configuration through two filters, one filter having a first set of pores sized so as to at least partially separate the enzyme from larger aggregates, and a second filter having a set of pores smaller than the first set which are sized so as to permit the detergent to pass through while retaining the enzyme on the second filter.

* * * * *